United States Patent
Seo et al.

(10) Patent No.: US 9,795,343 B2
(45) Date of Patent: *Oct. 24, 2017

(54) METHOD AND APPARATUS FOR PROVIDING BIOMETRIC INFORMATION

(71) Applicant: Samsung Electronics Co., Ltd., Gyeonggi-do (KR)

(72) Inventors: Hyung-jin Seo, Gyeonggi-do (KR); Jae-young Lee, Gyeonggi-do (KR); Sung-hyun Cho, Seoul (KR); Cory Kim, Gyeonggi-do (KR); Jong-eun Yang, Seoul (KR)

(73) Assignee: Samsung Electronics Co., Ltd. (KR)

( * ) Notice: Subject to any disclaimer, the term of this patent is extended or adjusted under 35 U.S.C. 154(b) by 63 days.

This patent is subject to a terminal disclaimer.

(21) Appl. No.: 14/920,531

(22) Filed: Oct. 22, 2015

(65) Prior Publication Data

US 2016/0038098 A1 Feb. 11, 2016

Related U.S. Application Data

(63) Continuation of application No. 12/871,291, filed on Aug. 30, 2010, now Pat. No. 9,183,356.

(30) Foreign Application Priority Data

Aug. 28, 2009 (KR) .................. 10-2009-0080723

(51) Int. Cl.
*A61B 5/00* (2006.01)
*A61B 5/021* (2006.01)
(Continued)

(52) U.S. Cl.
CPC ............ *A61B 5/742* (2013.01); *A61B 5/021* (2013.01); *A61B 5/4509* (2013.01);
(Continued)

(58) Field of Classification Search
None
See application file for complete search history.

(56) References Cited

U.S. PATENT DOCUMENTS

| | | |
|---|---|---|
| 5,546,943 A | 8/1996 | Gould |
| 6,839,455 B2 | 1/2005 | Kaufman |

(Continued)

FOREIGN PATENT DOCUMENTS

| | | |
|---|---|---|
| JP | 2004008659 | 1/2004 |
| JP | 2004041811 | 2/2004 |

(Continued)

OTHER PUBLICATIONS

Korean Office Action dated Sep. 18, 2015 issued in counterpart application No. 10-2009-80723, 11 pages.

*Primary Examiner* — Maurice L McDowell, Jr.
(74) *Attorney, Agent, or Firm* — The Farrell Law Firm, P.C.

(57) ABSTRACT

A method and apparatus for providing information are provided. The method includes measuring biometric information corresponding to a health condition of a body part of a user, determining a visual metaphor representation for characterizing a degree of the health condition based on mapping information between components of the visual metaphor representation and types of the measured biometric information, transforming, by a processor, the measured biometric information into the determined visual metaphor representation, and providing the transformed visual metaphor representation.

17 Claims, 6 Drawing Sheets

| | AIRPLANE | PLANT | TRAFFIC LIGHT |
|---|---|---|---|
| BONE DENSITY | RIGHT WING | STEMS | RED LIGHT |
| BLOOD PRESSURE | LEFT WING | LEAVES | ORANGE LIGHT |
| OBESITY LEVEL | PROPELLAR | FRUITS | BLUE LIGHT |

(51) Int. Cl.
  *G06T 7/00* (2017.01)
  *G06T 11/60* (2006.01)
  *G06F 19/00* (2011.01)

(52) U.S. Cl.
  CPC ........ *A61B 5/4866* (2013.01); *G06F 19/3487* (2013.01); *G06T 7/0012* (2013.01); *G06T 11/60* (2013.01); *G06F 19/321* (2013.01); *G06T 2207/10004* (2013.01); *G06T 2207/30196* (2013.01)

(56) References Cited

U.S. PATENT DOCUMENTS

| | | |
|---|---|---|
| 8,463,006 B2 | 6/2013 | Prokoski |
| 9,101,261 B2 | 8/2015 | Kim et al. |
| 9,183,356 B2 * | 11/2015 | Seo .................... G06F 19/3487 |
| 2003/0217294 A1 | 11/2003 | Kyle |
| 2005/0222638 A1 | 10/2005 | Foley et al. |
| 2006/0178661 A1 | 8/2006 | Neher et al. |
| 2009/0009284 A1 | 1/2009 | Sako |
| 2009/0024415 A1 | 1/2009 | Alpert et al. |
| 2009/0148020 A1 | 6/2009 | Sugiura |
| 2009/0175491 A1 | 7/2009 | Charpentier |
| 2009/0306511 A1 | 12/2009 | Yamagata |
| 2010/0204616 A1 | 8/2010 | Shears et al. |

FOREIGN PATENT DOCUMENTS

| | | |
|---|---|---|
| JP | 2008131977 | 6/2008 |
| KR | 10-2006-0032409 | 4/2006 |
| KR | 100657901 | 4/2006 |

* cited by examiner

[BONE DENSITY]

| MEASURED BODY PART | DISPLAY |
|---|---|
| FINGERS |  |
| ARM |  |
| RIBS |  |

[BONE DENSITY]

| MEASURED BODY PART | DISPLAY |
|---|---|
| FINGERS |  |
| ARM |  |
| RIBS |  |

| BLOOD PRESSURE | STRENGTH | TEMPERATURE |
|---|---|---|
| 150~ | 3 | 20 |
| 120~140 | 2 | 25 |
| 100~120 | 1 | 30 |

|  | AIRPLANE | PLANT | TRAFFIC LIGHT |
|---|---|---|---|
| BONE DENSITY | RIGHT WING | STEMS | RED LIGHT |
| BLOOD PRESSURE | LEFT WING | LEAVES | ORANGE LIGHT |
| OBESITY LEVEL | PROPELLAR | FRUITS | BLUE LIGHT |

METHOD AND APPARATUS FOR PROVIDING BIOMETRIC INFORMATION

PRIORITY

This application is a continuation of U.S. patent application Ser. No. 12/871,291 which was filed in the United States Patent and Trademark Office on Aug. 30, 2010, and which claims priority under 35 U.S.C. §119(a) to Korean Patent Application No. 10-2009-0080723, filed on Aug. 28, 2009, in the Korean Intellectual Property Office, the entire content of which is incorporated herein by reference.

BACKGROUND OF THE INVENTION

1. Field of the Invention

The present invention relates generally to a method and apparatus for providing information, and more particularly, to a method and apparatus for providing biometric information.

2. Description of the Related Art

As the number of people in poverty has been significantly decreasing and standards of living have been increasing, interest in health has been increasing. Accordingly, measurement and management of physical health status has become increasingly commonplace, regardless of age.

In particular, older people periodically measure their physical health status through health screening and understand their physical health status by examining numerical data.

SUMMARY OF THE INVENTION

The present invention provides a method and apparatus for effectively providing biometric information.

According to an aspect of the present invention, a method of providing information is provided. The method includes measuring biometric information corresponding to a health condition of a body part of a user, determining a visual metaphor representation for characterizing a degree of the health condition based on mapping information between components of the visual metaphor representation and types of the measured biometric information, transforming, by a processor, the measured biometric information into the determined visual metaphor representation, and providing the transformed visual metaphor representation.

According to another aspect of the present invention, an apparatus for providing information is provided. The apparatus includes a measuring unit and a display unit. The measuring unit is configured to measure biometric information corresponding to a health condition of a body part of a user, a processor configured to determine a visual metaphor representation for characterizing a degree of the health condition based on mapping information between components of the visual metaphor representation and types of the measured biometric information, and transform the measured biometric information into the determined visual metaphor representation. The display unit is configured to provide the transformed visual metaphor representation.

BRIEF DESCRIPTION OF THE DRAWINGS

The above and other features and advantages of the present invention will become more apparent by describing in detail embodiments thereof with reference to the attached drawings in which.

DETAILED DESCRIPTION OF THE INVENTION

The present invention will now be described more fully with reference to the accompanying drawings, in which embodiments of the invention are shown.

Figure 1:
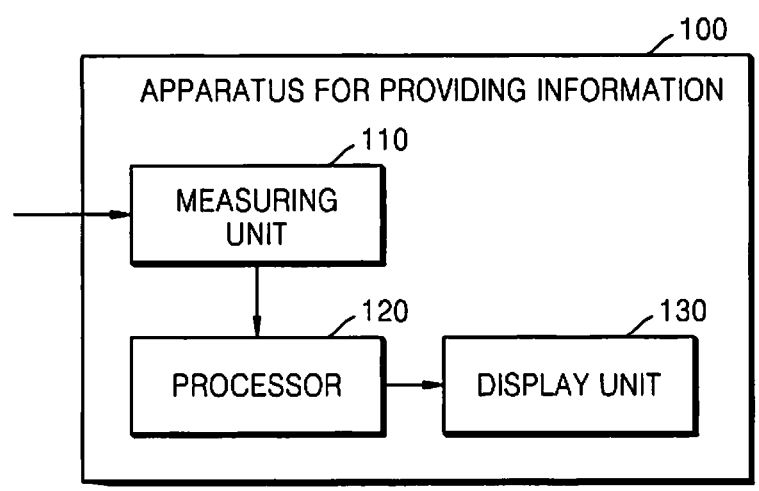
FIG. 1 is a block diagram of an apparatus for providing information, according to an embodiment of the present invention.

FIG. 1 is a block diagram of an apparatus 100 for providing information, according to an embodiment of the present invention.

Referring to FIG. 1, the apparatus 100 includes a measuring unit 110, a processor 120, and a display unit 130. The measuring unit 110 measures biometric information of a user. The biometric information may include any information about a user's body. For example, the biometric information may include at least one information item selected from a group including of blood pressure, pulse, electrocardiogram, heart rate, skin surface temperature, respiratory amount, weight, height, body movement, electromyogram, perspiration, and skin response.

The measuring unit 110 may further acquire information about a measured body part, the biometric information of which has been measured. For example, if blood pressure is measured by attaching a sensor to one of the arms of the user, blood pressure information is used as the biometric information, while the arm is the measured body part.

The processor 120 processes the biometric information. The biometric information measured by the measuring unit 110 is generally expressed through numerical data. The processor 120 enables the user to intuitively understand the biometric information expressed using the numerical data by transforming the numerical data into another form, such as sight, hearing, or touch.

The processor 120 may process the biometric information based on a type of the biometric information. If the biometric information is blood pressure, the processor 120 may visualize the blood pressure as veins and express the measurement of the blood pressure by using a degree of expansion or color of the veins. If the blood pressure is expressed using numerical data, the user may not intuitively understand the status of the blood pressure. However, if the blood pressure is expressed using a degree of expansion or color of the veins, the user may intuitively understand the status of the blood pressure.

The processor 120 may process the biometric information based on the measured body part. For example, if bone density is measured by attaching sensors to the fingers of the user, since the measured body part is the fingers, the processor 120 may visualize the bone density as finger bones. Likewise, if bone density is measured by attaching the sensor to the chest, since the measured body part is the chest, the processor 120 may visualize the bone density as ribs.

The processor 120 may also process the biometric information further based on profile information of the user. The profile information of the user may include any information related to the user, including, age, occupation, mental age, height, and family relationships. Accordingly, the processor 120 may change an object as which the biometric information is visualized based on the profile information of the user. For example, such an object change may occur for children, who may be repulsed by visualizations of finger bones or veins, as described above.

The processor 120 may process the biometric information so that the user may understand the biometric information by using sight, touch, hearing, or smell. A method of processing the biometric information to transfer the biometric information to the user by using touch is described herein with reference to FIG. 6.

The display unit 130 may display the biometric information on the measured body part. For example, if the measured body part is one of the hands of the user, the display unit 130 may display finger bones on a surface of the hand of the user or on the sensor by using a laser or a projector.

The display unit 130 displays the biometric information over image data obtained by photographing the measured body part. The display unit 130 may combine the image data corresponding with the measured body part with the biometric information to generate new image data, or may overlap the biometric information and the image data by using a laser or a projector.

If several pieces of image data are obtained by photographing the measured body part, a signal for selecting one of the several pieces of image data on which the biometric information is to be displayed may be received through an interface.

The apparatus 100 may further include a transmitting unit (not shown) or a receiving unit (not shown).

The receiving unit receives the image data from an external device connected through a network to the apparatus 100. The apparatus 100 may be connected through a wired network, such as Local Area Network (LAN), or a wireless network, such as High-Speed Downlink Packet Access (HSDPA) or Wireless BROadband (WiBro), to at least one external device (not shown).

The transmitting unit transmits the image data on which the biometric information processed by the processor 120 has been displayed to the external device through the network. The user may receive the transmitted image data through a receiving device, such as a computer or a mobile phone, and understand his/her health status by using the receiving device.

Figure 2:
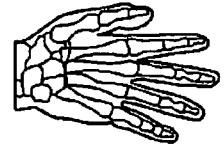
FIG. 2 is a table used by the apparatus of FIG. 1 to process biometric information, according to an embodiment of the present invention.
Figure 2:
Figure 2:

FIG. 2 is a table used by the apparatus 100 of FIG. 1 to process the biometric information, according to an embodiment of the present invention.

Referring to FIGS. 1 and 2, when bone density of the user is measured as biometric information, the processor 120 visualizes the bone density as bones so that the user may see and intuitively understand the status of his/her bone density. At this time, the processor 120 may change a color of the bones in order to indicate whether numerical data of the bone density is normal or abnormal.

The processor 120 may determine a type of bones to be visualized according to a measured body part, the bone density of which has been measured. For example, the processor 120 visualizes the bone density as finger bones if the bone density is measured by attaching the sensor to one of the hands of the user, the processor 120 visualizes the bone density as arm bones if the bone density is measured by attaching the sensor to one of the arms of the user, and the processor 120 visualizes the bone density as ribs if the bone density is measured by attaching the sensor to the chest of the user.

Figure 3:
FIG. 3 is a table used by the apparatus of FIG. 1 to process biometric information, according to another embodiment of the present invention.
Figure 3:
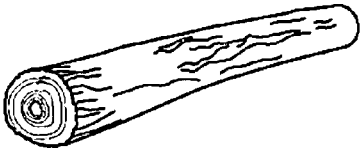
Figure 3:

FIG. 3 is a table used by the apparatus 100 of FIG. 1 to process the biometric information, according to another embodiment of the present invention.

Referring to FIG. 3, bone density of the user is also measured. However, in FIG. 3, an object as which the bone density is visualized is changed in consideration of the age of the user. For example, if the user is a child or another person who may feel repulsed by a visualization of a body part, the user may not prefer images of bones for a bone density visualization. In such a case, the processor 120 may visualize bone density as something that is not repulsive to the user.

Referring to the table of FIG. 3, if the measured body part includes fingers, for example, the bone density may be visualized as veins of a leaf, and if the measured body part is one of the arms, the bone density may be visualized as a log. Also, if the measured body part is ribs, the bone density may be visualized as umbrella ribs.

Bone density may be measured by attaching a sensor to a user's arm. If the bone density is normal, the bone density may be visualized as a solid log, and if the bone density is abnormal, the bone density may be visualized as a log with a hole. If the measured bone density is much less than a normal bone density value, the measured bone density may be visualized as a log having lots of holes, so that the user may intuitively understand his/her status.

Figure 4:
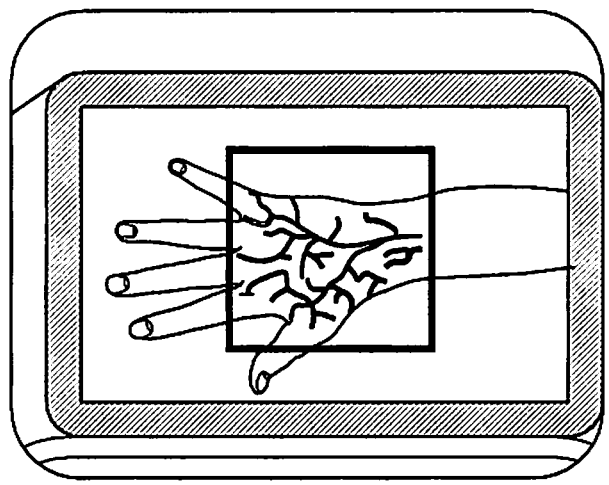
FIG. 4 is an example of an image displayed by the apparatus of FIG. 1, according to an embodiment of the present invention.

FIG. 4 is an example of an image displayed by the apparatus 100 of FIG. 1, according to an embodiment of the present invention.

Referring to FIG. 4, blood pressure may be measured by attaching a sensor a hand of the user. Accordingly, in this example, the hand is the measured body part and blood pressure is the biometric information.

The processor 120 visualizes the blood pressure as veins. If the measured blood pressure is high, the processor 120 visualizes the blood pressure as veins that are greatly expanded. However, if the measured blood pressure of the user is a normal value, the processor 120 visualizes the blood pressure as veins that are not expanded.

The display unit 130 directly displays the biometric information, which has been processed by the processor 120, on the hand of the user by using the projector. More specifically, the display unit 130 displays the veins on the hand of the user. The user may intuitively understand the status of his/her blood pressure by checking whether the veins visualized on the user's hand are expanded.

Figure 5:
FIG. 5 is an example of another image displayed by the apparatus of FIG. 1, according to another embodiment of the present invention.

FIG. 5 is an example of another image displayed by the apparatus 100 of FIG. 1, according to another embodiment of the present invention.

Referring to FIG. 5, a status of a user's teeth is measured by an X-ray. Accordingly, in this example, the teeth are the measured body part, and the status of the teeth the biometric information.

The processor 120 visualizes the status of the teeth as a worm. When, a status of the teeth is worse than the example depicted in FIG. 5, a larger worm or a greater number of worms may be displayed, so that a user may intuitively understand the status of his/her teeth.

The display unit 130 displays the biometric information, which has been processed by the processor 120, on an X-ray image obtained by photographing the user's teeth.

If the status of the teeth of the user is unhealthy, for example, if there is a decayed tooth or the teeth are not well taken care of, a worm may be added to the X-ray image of the teeth.

However, if the status of the teeth of the user is healthy, for example, if there are no decayed tooth and the teeth are well taken care of, a message indicating that the teeth are healthy may be displayed by on the X-ray image of the teeth.

Figures 6, 7:
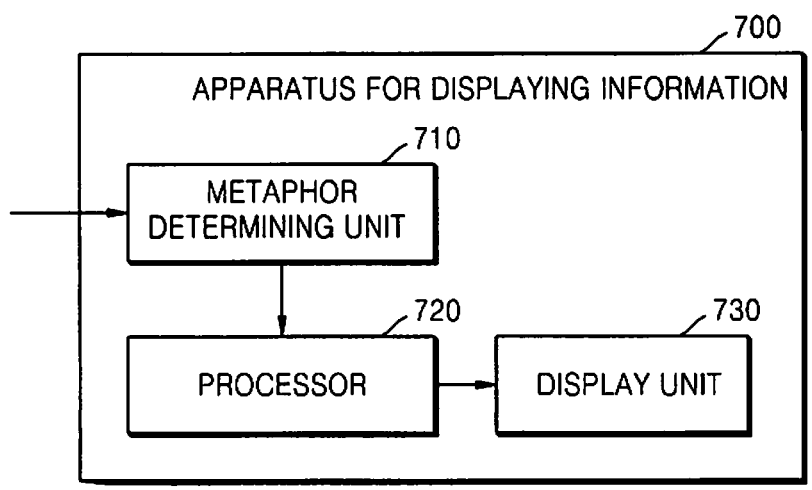
FIG. 6 is a table used by the apparatus of FIG. 1 to display biometric information, according to an embodiment of the present invention.
FIG. 7 is a block diagram of an apparatus for providing information, according to another embodiment of the present invention.

FIG. 6 is a table used by the apparatus 100 of FIG. 1 to display the biometric information in a case where the apparatus 100 transfers the biometric information to the user by using a touch according to an embodiment of the present invention.

Referring to FIGS. 1 and 6, the apparatus 100 measures blood pressure by attaching a sensor to an arm of a user, and displays an indication of blood pressure according to a change in temperature and pressure applied to the arm.

If the blood pressure of the user ranges from 100 to 120, no stimulus or only a weak stimulus may be applied to the arm of the user. When no stimulus or only a weak stimulus is applied to the arm of the user, the user may intuitively understand that his/her blood pressure is normal.

However, if the blood pressure of the user ranges from 120 to 140, a stimulus having twice a magnitude as the stimulus applied when the blood pressure is normal is applied to the user's arm and a temperature of the sensor is reduced to 25° C. The user may intuitively understand that his/her blood pressure is abnormal by recognizing that the temperature of the sensor has changed.

If the blood pressure of the user is greater than 150, a stimulus having three times the magnitude of the stimulus applied when the blood pressure is normal is applied to the arm of the user and the temperature of the sensor is reduced to a temperature lower than 20° C. The user can understand that his/her blood pressure is dangerous by recognizing that a stimulus applied to the arm of the user is large and recognizing that the arm is cooled by the temperature sensor.

FIG. 7 is a block diagram of an apparatus 700 for providing information, according to another embodiment of the present invention.

Referring to FIG. 7, the apparatus 700 includes a metaphor determining unit 710, a processor 720, and a display unit 730.

The metaphor determining unit 710 determines a metaphor through which biometric information is visualized. The metaphor determining unit 710 may display a metaphor list to the user and the user may select an item in the metaphor list.

The processor 720 visualizes the biometric information of the user as at least one component of the metaphor. The processor 720 may visualize the biometric information based on mapping information between the biometric information and the components of the metaphor. The mapping information between the biometric information and the components of the metaphor are described herein below with reference to FIG. 8.

The display unit 730 displays the biometric information that has been visualized by the processor 720.

Figures 8, 9:
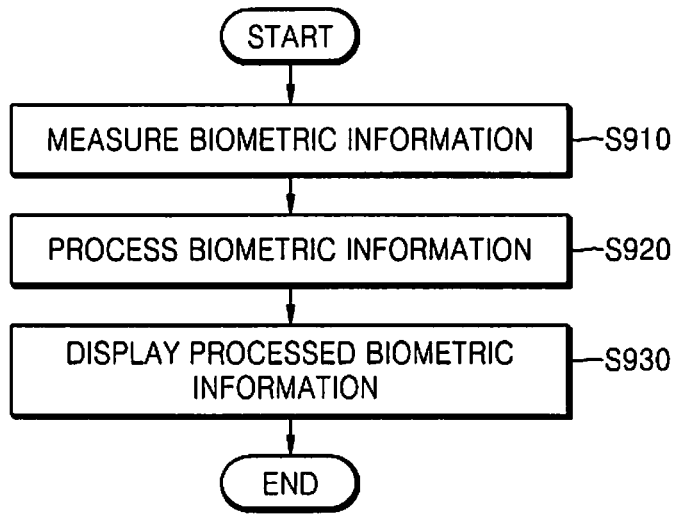
FIG. 8 is a table used by the apparatus of FIG. 7 to display biometric information.
FIG. 9 is a flowchart illustrating a method of providing information, according to an embodiment of the present invention.

FIG. 8 illustrates a mapping table between the biometric information and the metaphor used by the apparatus 700 of FIG. 7 to display the biometric information, according to an embodiment of the present invention.

For example, a user may select one of an airplane, a plant, and a traffic light as the metaphor. If the user selects the airplane as the metaphor, bone density may be displayed as a right wing of the airplane, blood pressure may be displayed as a left wing of the airplane, and obesity level may be displayed as a propeller. If the bone density is abnormal, the apparatus 100 may display the airplane as if smoke is rising up from the right wing of the airplane. The apparatus 100 may display more smoke rising up from the right wing as the bone density worsens.

If the user selects the plant as the metaphor, the bone density of the user may be displayed as stems, the blood pressure of the user may be displayed as leaves, and the obesity level of the user may be displayed as fruits. For example, if the blood pressure is abnormal, the apparatus 100 may display the plant as if the leaves of the plant are dry and drooping downwards. In particular, the apparatus 100 may display a greater number of leaves drooping downwards as the blood pressure worsens.

If the user selects the traffic light as the metaphor, the bone density of the user may be displayed as a red light, the blood pressure of the user may be displayed an orange light, and the obesity level of the user may be displayed as a blue light. For example, if the obesity level of the user is abnormal, the apparatus 100 may reduce the displayed intensity of the traffic light. More specifically, the apparatus 100 may reduce the displayed intensity of the traffic light as the obesity level of the user worsens.

FIG. 9 is a flowchart illustrating a method of providing information, according to an embodiment of the present invention.

In step S910, biometric information of a user is measured.

In step S920, the biometric information is processed based on at least one item selected from a group including a type of the biometric information, a measured body part, the biometric information of which has been measured, and a profile of the user.

In step S930, the biometric information is displayed on the measured body part or the biometric information is added to image data obtained by photographing the measured body part. If a plurality of pieces of image data is obtained by photographing the measured body part, one piece of the obtained image data on which the biometric information is to be displayed may be selected. The image data to which the biometric information is added may be transmitted to an external device through a network, and the user may directly understand the biometric information by using the external device. The user may understand the biometric information by using sight, hearing, or touch.

Figure 10:
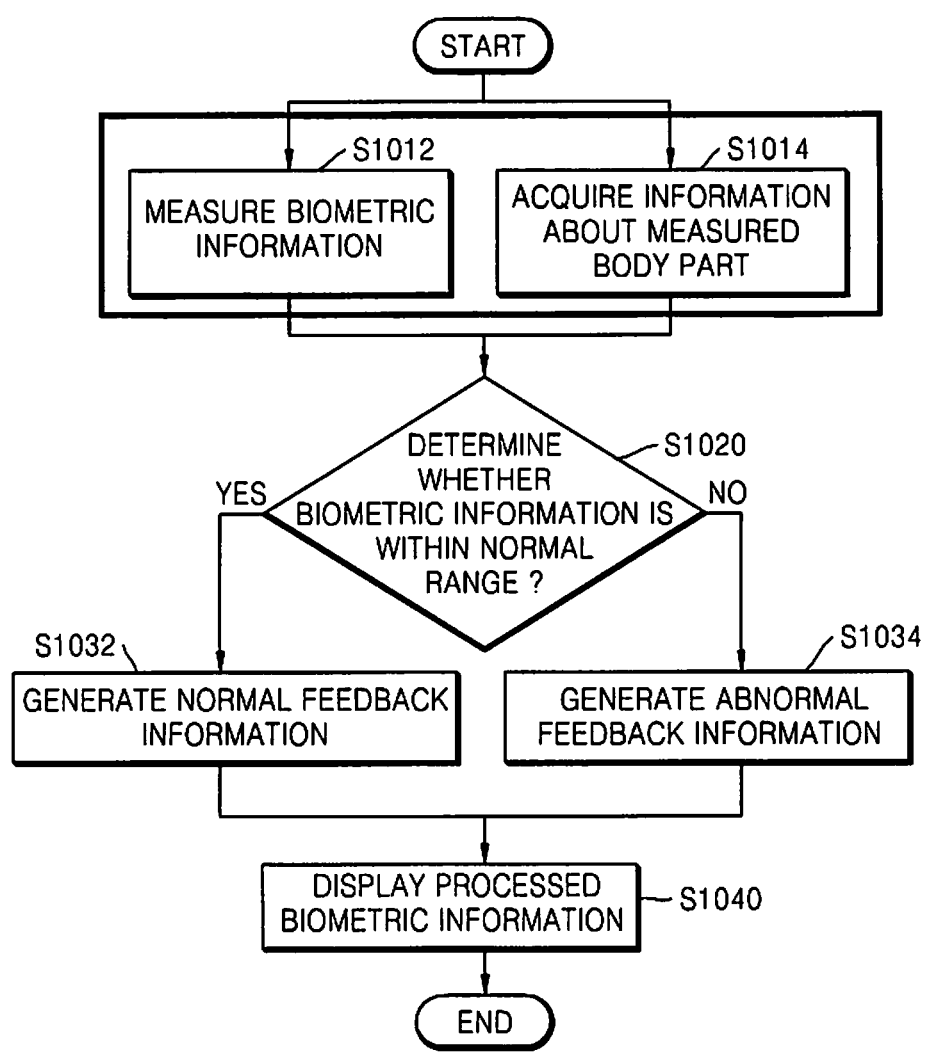
FIG. 10 is a flowchart illustrating a method of providing information, according to another embodiment of the present invention.

FIG. 10 is a flowchart illustrating a method of providing biometric information to a user, according to another embodiment of the present invention.

Referring to FIG. 10, in step S1012, biometric information of a user is measured. In step S1014, information about a measured body part, the biometric information of which has been measured, is acquired. In step S1020, it is determined whether the biometric information is within a normal range. If the biometric information is within the normal range, the method proceeds to step S1032. Otherwise, the method proceeds to step S1034.

In step S1032, the biometric information is processed so that the user may intuitively know that the biometric information is normal. In step S1034, the biometric information is processed so that the user may intuitively know that the biometric information is abnormal. In step S1040, the processed biometric information is displayed.

Various embodiments of the present invention may be implemented through computer programs executed in general-use digital computers using a computer readable recording medium. Examples of computer readable recording mediums include magnetic storage media (e.g., Read Only Memory (ROM), floppy disks, hard disks, etc.), optical recording media (e.g., Compact Disc (CD)-ROMs, or Digital Versatile Discs (DVDs)), etc.

While this invention has been particularly shown and described with reference to embodiments thereof, it will be understood by those skilled in the art that various changes in form and details may be made therein without departing from the spirit and scope of the invention as defined by the appended claims. Embodiments should be considered in descriptive sense only and not for purposes of limitation. Accordingly, the scope of the invention is defined not by the detailed description of the invention but by the appended claims, and all differences within the scope of the claims will be construed as being included in the present invention.

What is claimed is:

1. A method of providing information, the method comprising:
   measuring biometric information corresponding to a health condition of a body part of a user;
   determining a visual metaphor representation for characterizing a degree of the health condition based on mapping information between components of the visual metaphor representation and types of the measured biometric information;
   transforming, by a processor, the measured biometric information into the determined visual metaphor representation; and
   providing the transformed visual metaphor representation.

2. The method of claim 1, further comprising generating, by the processor, an image in which the determined visual metaphor representation is reflected on an object visualizing the body part to identify the health condition,
   wherein providing the transformed visual metaphor representation comprises providing the measured biometric information by displaying the generated image.

3. The method of claim 2, further comprising transmitting the generated image to an external device through a network.

4. The method of claim 1, further comprising processing, by the processor, the biometric information based on profile information of the user.

5. The method of claim 1, further comprising adjusting, by the processor, strength of a stimulus applied to the body part based on the biometric information.

6. The method of claim 1, further comprising selecting an image in which the biometric information is to be reflected from among a plurality of images obtained by photographing the body part.

7. The method of claim 1, further comprising receiving an image in which the biometric information is to be reflected, wherein the received image is obtained by photographing the body part from an external device connected through a network.

8. The method of claim 1, wherein the biometric information includes one of electrocardiogram information, electroencephalogram information, stress level information, bone mineral density information, body mass index information, calories burned information, and physical age information.

9. An apparatus for providing information, the apparatus comprising:
   a measuring unit configured to measure biometric information corresponding to a health condition of a body part of a user;
   a processor configured to determine a visual metaphor representation for characterizing a degree of the health condition based on mapping information between components of the visual metaphor representation and types of the measured biometric information, and transform the measured biometric information into the determined visual metaphor representation; and
   a display unit configured to provide the transformed visual metaphor representation.

10. The apparatus of claim 9, wherein the processor is further configured to generate an image in which the visual metaphor representation is reflected on an object visualizing the body part to identify the health condition,
    wherein the display unit is configured to provide the measured biometric information by displaying the generated image.

11. The apparatus of claim 10, further comprising a transmitting unit configured to transmit the generated image on which the biometric information has been displayed to an external device through a network.

12. The apparatus of claim 9, wherein the processor is further configured to process the biometric information based on profile information of the user.

13. The apparatus of claim 9, wherein the display unit includes a control unit configured to adjust strength of a stimulus applied to the body part according to the biometric information.

14. The apparatus of claim 9, wherein the display unit includes a control unit configured to select an image in which the biometric information is to be reflected from among a plurality of images obtained by photographing the body part.

15. The apparatus of claim 9, further comprising a receiving unit configured to receive an image in which the biometric information is to be reflected, wherein the received image is obtained by photographing the body part from an external device connected to the apparatus through a network.

16. The apparatus of claim 9, wherein the biometric information includes one of electrocardiogram information, electroencephalogram information, stress level information, bone mineral density information, body mass index information, calories burned information, and physical age information.

17. A non-transitory recording medium having embodied thereon a program for executing a method of providing information, the method comprising:
    measuring biometric information corresponding to a health condition of a body part of a user;
    determining a visual metaphor representation for characterizing a degree of the health condition based on mapping information between components of the visual metaphor representation and types of the measured biometric information;

transforming the measured biometric information into the determined visual metaphor representation; and providing the transformed visual metaphor representation.

\* \* \* \* \*